US011262561B2

(12) United States Patent
Kato

(10) Patent No.: US 11,262,561 B2
(45) Date of Patent: Mar. 1, 2022

(54) RELAY LENS AND METHOD OF MANUFACTURING RELAY LENS

(71) Applicant: OLYMPUS CORPORATION, Hachioji (JP)

(72) Inventor: Takayuki Kato, Tokyo (JP)

(73) Assignee: OLYMPUS CORPORATION, Tokyo (JP)

(*) Notice: Subject to any disclaimer, the term of this patent is extended or adjusted under 35 U.S.C. 154(b) by 342 days.

(21) Appl. No.: 16/400,871

(22) Filed: May 1, 2019

(65) Prior Publication Data
US 2019/0258034 A1 Aug. 22, 2019

Related U.S. Application Data

(63) Continuation of application No. PCT/JP2017/044671, filed on Dec. 13, 2017.

(30) Foreign Application Priority Data

Dec. 28, 2016 (JP) .............................. JP2016-254727

(51) Int. Cl.
*G02B 13/00* (2006.01)
*G02B 7/02* (2021.01)
(Continued)

(52) U.S. Cl.
CPC ............ *G02B 13/0095* (2013.01); *A61B 1/00* (2013.01); *A61B 1/002* (2013.01); *G02B 7/02* (2013.01);
(Continued)

(58) Field of Classification Search
CPC ...... G02B 13/0095; G02B 13/00; G02B 7/02; G02B 7/021; G02B 23/2446; G02B 23/26; G02B 27/0025; A61B 1/00; A61B 1/002
(Continued)

(56) References Cited

U.S. PATENT DOCUMENTS 4,779,613 A * 10/1988 Hashiguchi ........ A61B 1/00179
359/512
5,142,410 A * 8/1992 Ono ................... G02B 23/2446
359/434
(Continued)

FOREIGN PATENT DOCUMENTS

JP S61282815 A 12/1986
JP H02272512 A 11/1990
(Continued)

OTHER PUBLICATIONS

International Search Report (ISR) dated Mar. 20, 2018 issued in International Application No. PCT/JP2017/044671.
(Continued)

*Primary Examiner* — Collin X Beatty
(74) *Attorney, Agent, or Firm* — Holtz, Holtz & Volek PC

(57) ABSTRACT

Provided is a relay lens including a plurality of relay optical systems that are arranged in a long, rigid tube along a longitudinal direction and that re-form an image, wherein each of the relay optical systems includes a pair of rod lenses that are disposed with a space therebetween in the longitudinal direction, a barrel that is disposed between the pair of rod lenses along the longitudinal direction, and a positive lens that is fixed to an inner side of the barrel and that has a positive refractive power; and a length of the barrel in the longitudinal direction is larger than a thickness of a peripheral edge of the positive lens in the longitudinal direction.

2 Claims, 6 Drawing Sheets

(51) Int. Cl.
  *G02B 23/24* (2006.01)
  *G02B 27/00* (2006.01)
  *G02B 23/26* (2006.01)
  *A61B 1/002* (2006.01)
  *A61B 1/00* (2006.01)

(52) U.S. Cl.
  CPC ............ *G02B 7/021* (2013.01); *G02B 13/00* (2013.01); *G02B 23/2446* (2013.01); *G02B 23/26* (2013.01); *G02B 27/0025* (2013.01)

(58) Field of Classification Search
  USPC .......................................................... 359/434
  See application file for complete search history.

(56) References Cited

U.S. PATENT DOCUMENTS

| | | | |
|---|---|---|---|
| 5,206,759 | A | 4/1993 | Ono et al. |
| 5,632,718 | A * | 5/1997 | Igarashi ................. A61B 1/002 |
| | | | 359/434 |
| 5,902,232 | A | 5/1999 | Igarashi |
| 6,471,640 | B1 | 10/2002 | Frische et al. |
| 8,773,765 | B2 * | 7/2014 | Sasamoto ................. G02B 7/36 |
| | | | 359/684 |
| 2003/0179448 | A1 * | 9/2003 | Ramsbottom .......... G02B 23/26 |
| | | | 359/435 |
| 2004/0252386 | A1 * | 12/2004 | Lei ..................... G02B 23/2446 |
| | | | 359/754 |
| 2012/0071721 | A1 * | 3/2012 | Remijan ............ G02B 23/2469 |
| | | | 600/121 |
| 2016/0274443 | A1 * | 9/2016 | Ogata .................... G03B 17/14 |

FOREIGN PATENT DOCUMENTS

| | | |
|---|---|---|
| JP | H07005377 A | 1/1995 |
| JP | H08122667 A | 5/1996 |
| JP | 2002540454 A | 11/2002 |
| JP | 2005017615 A | 1/2005 |
| JP | 2007133175 A | 5/2007 |

OTHER PUBLICATIONS

Written Opinion dated Mar. 20, 2018 issued in International Application No. PCT/JP2017/044671.

* cited by examiner

RELAY LENS AND METHOD OF MANUFACTURING RELAY LENS

CROSS-REFERENCE TO RELATED APPLICATIONS

This is a continuation of International Application PCT/JP2017/044671 which is hereby incorporated by reference herein in its entirety.

This application is based on Japanese Patent Application No. 2016-254727, the contents of which are incorporated herein by reference.

TECHNICAL FIELD

The present invention relates to a relay lens and a method of manufacturing the relay lens.

BACKGROUND ART

In the related art, a relay lens that relays an object image from an objective optical system at the distal end of an insertion portion to an eyepiece optical system on the proximal end side of the insertion portion is used in a rigid scope (for example, see Patent Literatures 1 to 3). The relay lens is constituted of a plurality of lenses arranged in a long, small-diameter tube.

Meanwhile, there has been a demand for improvement in the resolving power of rigid scopes with the increasing resolution of cameras in recent years. The resolving power of a rigid scope can be improved by increasing the numerical aperture.

CITATION LIST

Patent Literature

{PTL 1} Japanese Unexamined Patent Application, Publication No. Hei 7-5377
{PTL 2} Japanese Unexamined Patent Application, Publication No. Hei 8-122667
{PTL 3} Japanese Unexamined Patent Application, Publication No. 2007-133175

SUMMARY OF INVENTION

A first aspect of the present invention is a relay lens including a plurality of relay optical systems that are arranged in a long, rigid tube along a longitudinal direction and that re-form an image, wherein: each of the relay optical systems includes: a pair of rod lenses that are disposed with a space therebetween in the longitudinal direction; a barrel that is disposed between the pair of rod lenses along the longitudinal direction; and a positive lens that is fixed to an inner side of the barrel and that has a positive refractive power, and a length of the barrel in the longitudinal direction is larger than a thickness of a peripheral edge of the positive lens in the longitudinal direction.

A second aspect of the present invention is a method of manufacturing a relay lens including a plurality of relay optical systems that are arranged in a long, rigid tube along a longitudinal direction and that re-form an image, wherein each of the relay optical systems includes a pair of rod lenses that are disposed with a space therebetween in the longitudinal direction, a barrel that is disposed between the pair of rod lenses along the longitudinal direction, and a positive lens that is fixed to an inner side of the barrel and that has a positive refractive power, the method including: a step of fixing the positive lens to the inner side of the barrel; and a step of processing an end face of the barrel, to which the positive lens is fixed on the inner side thereof, so as to be perpendicular to an optical axis of the positive lens.

A third aspect of the present invention is a method of manufacturing a relay lens including a plurality of relay optical systems that are arranged in a long, rigid tube along a longitudinal direction and that re-form an image, wherein each of the relay optical systems includes a pair of rod lenses that are disposed with a space therebetween in the longitudinal direction, a barrel that is disposed between the pair of rod lenses along the longitudinal direction, and a positive lens that is fixed to an inner side of the barrel and that has a positive refractive power, the method including: a step of fixing the positive lens to the inner side of the barrel; and a step of processing an outer circumferential surface of the barrel, to which the positive lens is fixed on the inner side thereof, so that a central axis of the outer circumferential surface coincides with an optical axis of the positive lens.

DESCRIPTION OF EMBODIMENT

A relay lens 1 according to an embodiment of the present invention will be described below with reference to the drawings.

Figure 1:
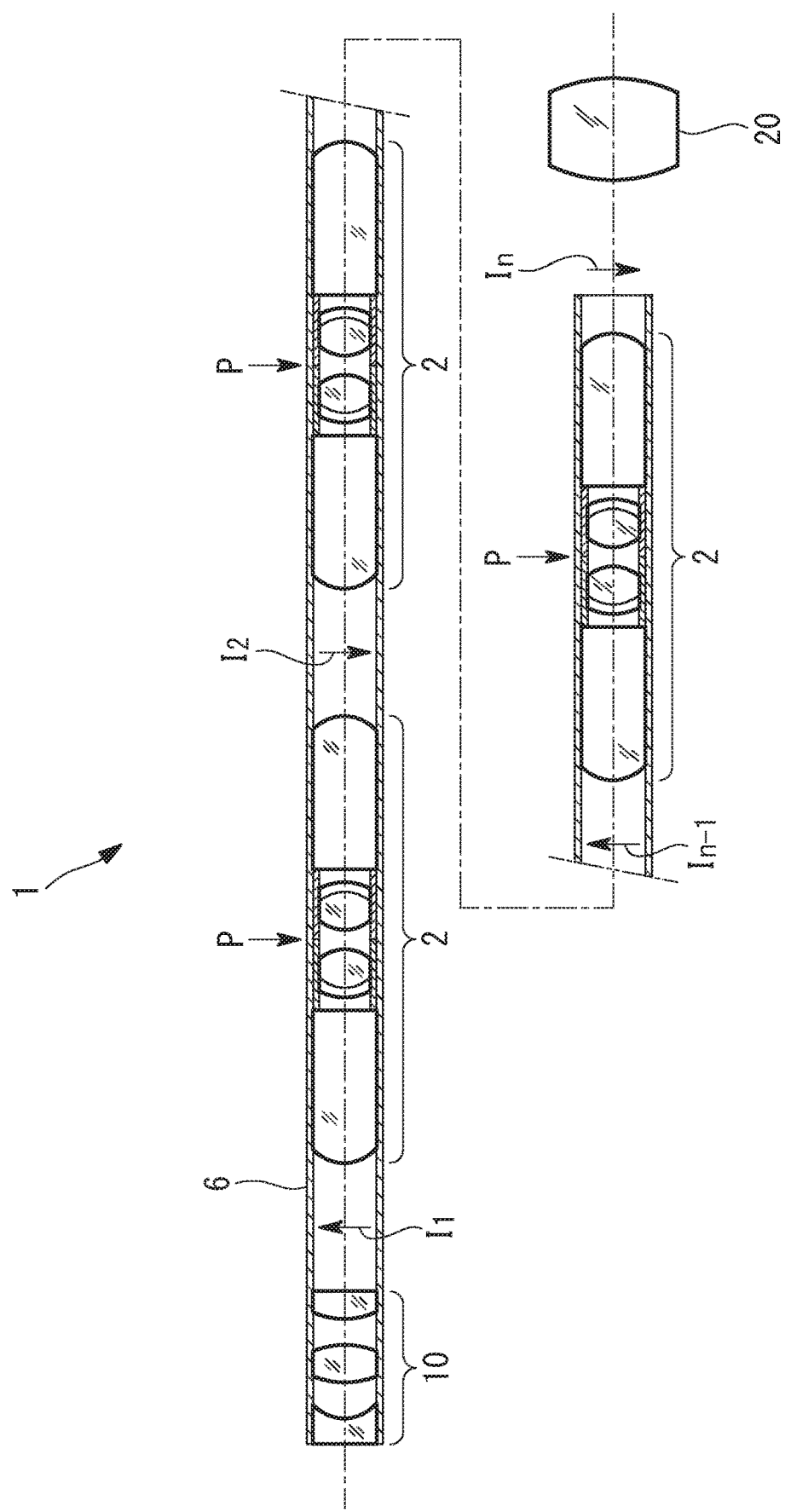
FIG. 1 is an overall configuration diagram of a relay lens according to an embodiment of the present invention.

The relay lens 1 according to this embodiment is installed in an elongated insertion portion provided in a rigid scope and, as shown in FIG. 1, relays an object image $I_1$ formed by an objective optical system 10 at the distal end of the insertion portion to an eyepiece optical system 20 provided on the proximal end side of the insertion portion.

The relay lens 1 includes a plurality of relay optical systems 2 that are arranged along the longitudinal direction of a rigid tube 6 which is a long and cylinder-shaped.

Figure 2:
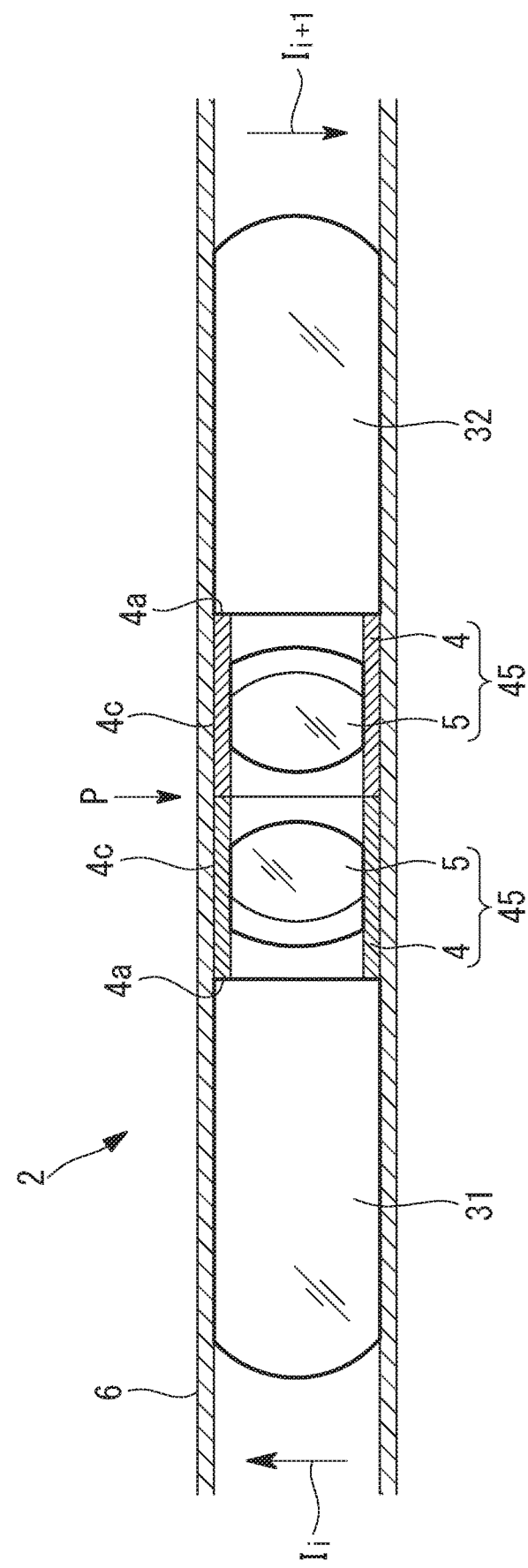
FIG. 2 is a configuration diagram of a relay optical system in the relay lens in FIG. 1.

As shown in FIG. 2, each of the relay optical systems 2 includes: a pair of rod lenses 31, 32 that are disposed with a space therebetween in the longitudinal direction of the tube 6; barrels 4 that are disposed between the pair of rod lenses 31, 32; and positive lenses 5 that are fixed in the barrels 4 and that have a positive refractive power. Each of the relay optical systems 2 forms an optical image $I_{i+1}$ by re-forming, at an equal magnification by means of the rod lenses 31, 32 and the positive lenses 5, an optical image $I_i$ ($i=1, 2, \ldots, n-1$) formed by the immediately preceding objective optical system 10 or by another relay optical system 2. The reference sign $I_n$ indicates a final image relayed by the relay lens 1, and the reference sign P indicates the position of a pupil of each of the relay optical systems 2.

Each of the rod lenses 31, 32 is a columnar lens having a flat surface, which is perpendicular to the long axis thereof, at one end on the pupil P side and having a convex surface at the other end on the opposite side from the pupil P, and has an outer diameter substantially equal to the inner diameter of the tube 6. The pair of rod lenses 31, 32 are arranged symmetrically, in the longitudinal direction, with respect to the pupil P positioned between the pair of rod lenses 31, 32.

The barrels 4 are disposed in the tube 6 along the longitudinal direction and have openings at both ends. Each of the barrels 4 has an outer diameter equal to the outer diameter of the rod lens 31, 32 and has an inner diameter substantially equal to the outer diameter of the positive lens 5. Among two end faces 4a, 4b of the barrel 4, at least the end face 4a adjacent to the flat surface of the rod lens 31, 32 is formed so as to be perpendicular to the optical axis of the positive lens 5.

Each of the positive lenses 5 is a cemented lens that is formed of a plurality of lenses joined together and that is suitable for correcting chromatic aberration. The positive lens 5 is fixed to the inner circumferential surface of the barrel 4 at the peripheral edge thereof. As shown in FIG. 2, in a case in which a plurality of the positive lenses 5 are provided between the pair of rod lenses 31, 32, the same number of the barrels 4 as the positive lenses 5 are provided, and the individual positive lenses 5 are fixed in the separate barrels 4. Alternatively, the plurality of positive lenses 5 may be fixed in a single barrel 4.

Figure 3:
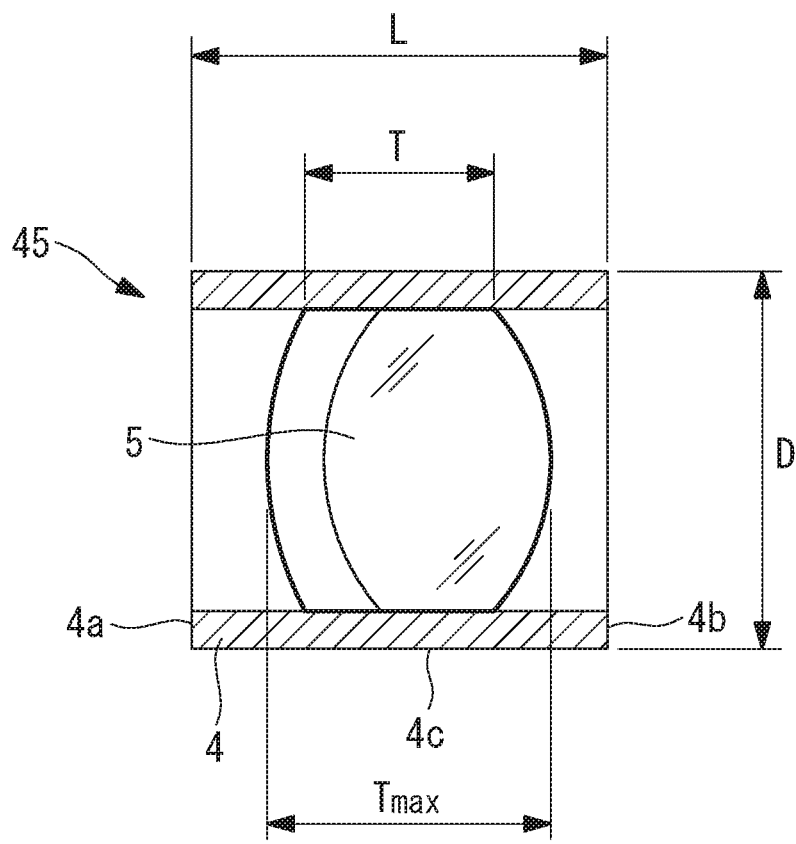
FIG. 3 is a diagram showing a unit composed of a barrel and a positive lens fixed in the barrel.

As shown in FIG. 3, the length L of the barrel 4 in the longitudinal direction is larger than the maximum thickness Tmax of the positive lens 5 in the optical-axis direction, the entirety of the positive lens 5 is disposed in the barrel 4, and both ends of the barrel 4 protrude farther than both lens surfaces of the positive lens 5. With this configuration, the barrel 4 also functions as a spacer for securing a space between the two positive lenses 5 as well as between the positive lenses 5 and the rod lenses 31, 32.

Figure 4:
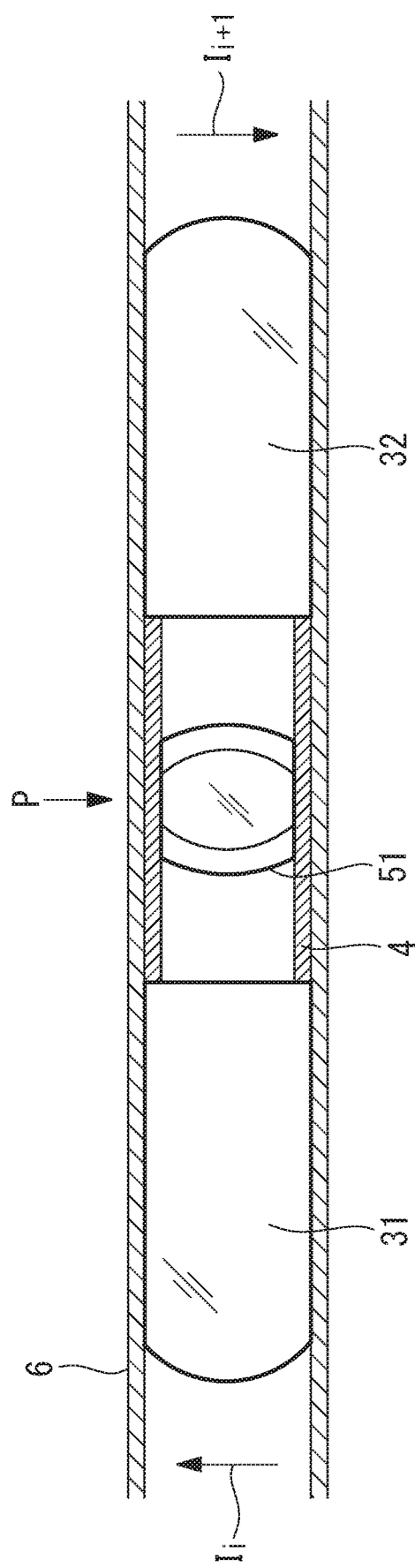
FIG. 4 is a configuration diagram of a modification of the relay optical system in FIG. 2.
Figure 5:
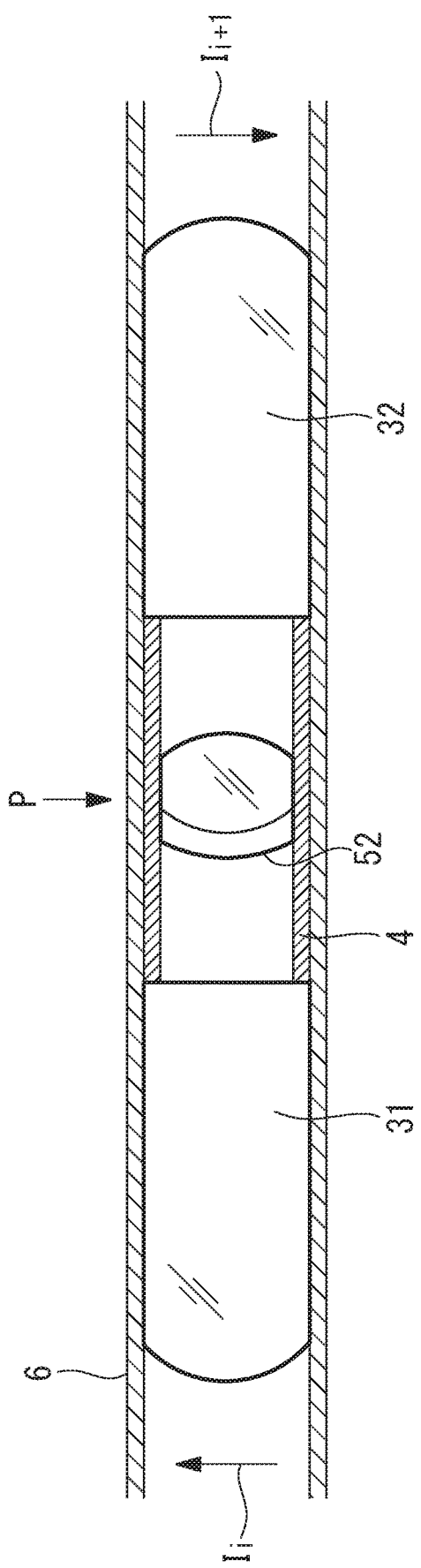
FIG. 5 is a configuration diagram of another modification of the relay optical system in FIG. 2.

Although FIG. 2 shows the two positive lenses 5 each formed of a cemented lens, the type and number of the positive lenses disposed between the rod lenses 31, 32 can be appropriately changed. For example, as shown in FIGS. 4 and 5, a single cemented lens 51, 52 formed of three or two lenses may be employed, or a positive lens formed of a single lens may be employed.

Next, a method of manufacturing the relay lens 1 will be described.

The method of manufacturing the relay lens 1 according to this embodiment includes: a first step of forming a unit 45 composed of the barrel 4 and the positive lens 5 by fixing the positive lens 5 to the inner side of the barrel 4; a second step of processing, among the two end faces 4a, 4b of the barrel 4 to which the positive lens 5 is fixed in the first step, at least the end face 4a on the side adjacent to the flat surface of the rod lens 31, 32; and a third step of assembling the rod lenses 31, 32 and the unit 45 into the tube 6.

In the first step, the peripheral edge of the positive lens 5 is fixed to the inner circumferential surface of the barrel 4 in such a manner that the optical axis of the positive lens 5 becomes parallel to the central axis of the barrel 4, whereby the unit 45 is formed.

Figure 6:
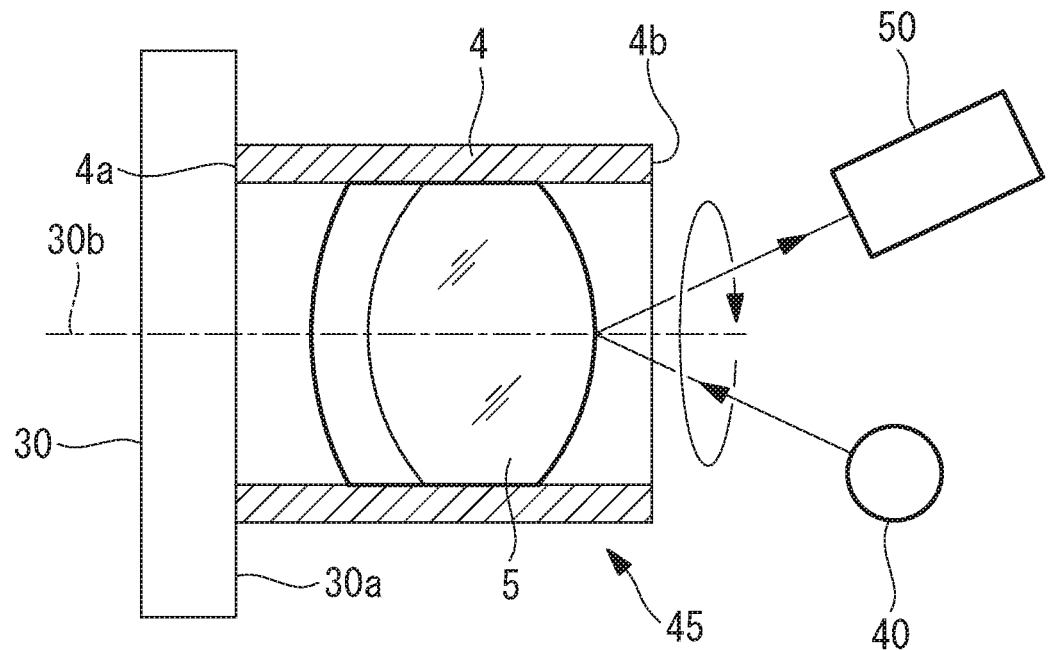
FIG. 6 is a diagram for explaining a step of grinding an end face of the barrel of the relay optical system in a method of manufacturing the relay lens according to the embodiment of the present invention.

Next, in the second step, as shown in FIG. 6, the optical axis of the positive lens 5 is made coincident with a rotation axis 30b, which is perpendicular to a grinding surface 30a of a grinding wheel 30, and by rotating the unit 45 about the rotation axis 30b in this state, the end face 4a of the barrel 4 is ground with the grinding surface 30a. By doing so, it is possible to process the end face 4a so that the end face 4a becomes perpendicular to the optical axis of the positive lens 5. The positioning of the optical axis of the positive lens 5 with respect to the rotation axis 30b can be performed by: radiating light from a light source 40 onto the rotating positive lens 5; detecting the position of reflected light from the positive lens 5 by means of a detector 50; and adjusting the position and tilting of the unit 45 so that the position of the reflected light becomes constant.

Next, in the third step, the rod lenses 31, 32 and the unit 45 manufactured in the first and second steps are inserted into the tube 6 in such a manner that the unit 45 is sandwiched between the pair of rod lenses 31, 32. Then, the position and the orientation of the barrel 4 inside the tube 6 are determined by abutting the end face 4a of the barrel 4 against the flat surface of the adjacent rod lens 31 or 32.

Here, because the tube 6 has a length corresponding to substantially the entire length of the insertion portion of the rigid scope, it is difficult to manufacture the tube 6 so as to have an inner diameter that is uniform over the entire length thereof, and manufacturing variations within the range of tolerances occur in the inner diameter of the tube 6. Assuming a case in which the positive lens 5 is inserted into the tube 6 as a single unit so that the peripheral edge of the positive lens 5 is in direct contact with the inner circumferential surface of the tube 6, tilting of the positive lens 5 inside the tube 6 is likely to occur due to a gap between the peripheral edge of the positive lens 5 and the inner circumferential surface of the tube 6. The tilting of the positive lens 5 located in the vicinity of the pupil P becomes the main cause of axial comatic aberration that occurs in the light relayed by the relay lens 1. Therefore, in order to improve the optical performance of the relay lens 1, it is important to suppress tilting of the positive lens 5 inside the tube 6 and to dispose the positive lens 5 in such a manner that the optical axis of the positive lens 5 becomes parallel to the longitudinal direction of the tube 6.

With this embodiment, because the barrel 4 has the length L which is larger than the maximum thickness Tmax of the positive lens 5, in the longitudinal direction of the tube 6, tilting of the barrel 4 inside the tube 6, which is caused by the variation in the inner diameter of the tube 6, is suppressed, and as a result, it is possible to suppress tilting of the positive lens 5 fixed in the barrel 4. With this configuration, even in a case in which the relay lens 1 is combined with an objective optical system 10 having a large numerical aperture, it is possible to suppress the occurrence of axial comatic aberration.

Furthermore, tilting inside the tube 6 hardly occurs with the rod lens 31, 32 having the long axis in the longitudinal direction of the tube 6, and the rod lens 31, 32 is disposed parallel to the longitudinal direction of the tube 6. By abutting the end face 4a of the barrel 4, the end face 4a being processed so as to be perpendicular to the optical axis of the positive lens 5, against the flat surface of the rod lens 31, 32, it is possible to determine the orientation of the barrel 4 and the positive lens 5 with respect to the tube 6 in such a manner that the optical axis of the positive lens 5 becomes parallel to the longitudinal direction of the tube 6, thereby suppressing tilting of the positive lens 5 to a higher degree.

Although the length L of the barrel 4 is set to be larger than the maximum thickness Tmax of the positive lens 5 in this embodiment, in order to obtain an effect of suppressing tilting of the positive lens 5 by providing the barrel 4, it suffices that the length L of the barrel 4 be larger than the thickness T (see FIG. 3) of the peripheral edge of the positive lens 5 in the optical-axis direction.

In addition, it is preferable that the length L of the barrel 4 satisfy Expression (1) below. D indicates the outer diameter of the barrel 4.

$$D \leq L \leq 3D \tag{1}$$

The larger the length L of the barrel 4, the larger the dimensional tolerances of the inner diameter and the outer diameter of the barrel 4, thus also increasing manufacturing errors in the inner diameter and the outer diameter of the barrel 4. By limiting the length L relative to the outer diameter D so as to satisfy Conditional Expression (1), it is possible to reduce the dimensional tolerances of the inner diameter and the outer diameter D of the barrel 4 and the manufacturing errors therein, and to enhance the effect of suppressing tilting of the positive lens 5.

In this embodiment, as with the positive lens 5, the rod lenses 31, 32 may also be accommodated in barrels separate from the barrel 4.

The method of manufacturing the relay lens 1 according to this embodiment may include, before the third step, instead of or in addition to the second step, a fourth step of processing an outer circumferential surface 4c of the barrel 4 to which the positive lens 5 is fixed in the first step.

Figure 7:
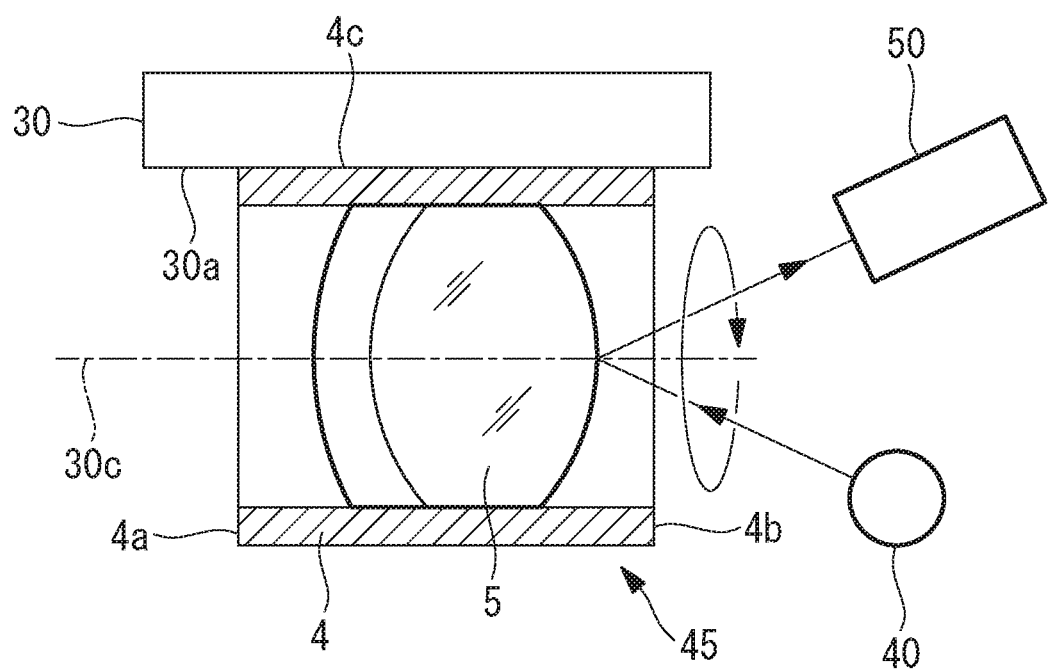
FIG. 7 is a diagram for explaining a step of grinding an outer circumferential surface of the barrel of the relay optical system in a method of manufacturing the relay lens according to the embodiment of the present invention.

In the fourth step, as shown in FIG. 7, the optical axis of the positive lens 5 is made coincident with a rotation axis 30c, which is parallel to the grinding surface 30a of the grinding wheel 30, and by rotating the unit 45 about the rotation axis 30c in this state, the outer circumferential surface 4c of the barrel 4 is ground with the grinding surface 30a. By doing so, it is possible to process the outer circumferential surface 4c so that the central axis of the outer circumferential surface 4c coincides with the optical axis of the positive lens 5. The positioning of the optical axis of the positive lens 5 with respect to the rotation axis 30c can be performed by: radiating light from the light source 40 onto the rotating positive lens 5; detecting the position of reflected light from the positive lens 5 by means of the detector 50; and adjusting the position and tilting of the unit 45 so that the position of the reflected light becomes constant.

As described above, by forming the outer circumferential surface 4c of the barrel 4 so as to be coaxial with the optical axis of the positive lens 5, it is possible to dispose the unit 45 in the tube 6 in such a manner that the optical axis of the positive lens 5 becomes parallel to the longitudinal direction of the tube 6 merely by inserting the unit 45 into the tube 6, thereby suppressing tilting of the positive lens 5.

The above-described embodiment leads to the following inventions.

A first aspect of the present invention is a relay lens including a plurality of relay optical systems that are arranged in a long, rigid tube along a longitudinal direction and that re-form an image, wherein: each of the relay optical systems includes: a pair of rod lenses that are disposed with a space therebetween in the longitudinal direction; a barrel that is disposed between the pair of rod lenses along the longitudinal direction; and a positive lens that is fixed to an inner side of the barrel and that has a positive refractive power, and a length of the barrel in the longitudinal direction is larger than a thickness of a peripheral edge of the positive lens in the longitudinal direction.

With this aspect, it is possible to relay an object image formed on one side of the tube by means of an objective optical system, etc. to the other side of the tube by means of the plurality of relay optical systems arranged in the tube.

In this case, the positive lens that is disposed in the vicinity of a pupil positioned between the pair of rod lenses is fixed in the barrel. Because the barrel has a length larger than the thickness of the peripheral edge of the positive lens, tilting of the barrel inside the tube is suppressed compared to tilting of the positive lens in a case in which the positive lens is directly fixed to the inner circumferential surface of the tube without providing a barrel, and as a result, tilting of the positive lens in the barrel is also suppressed. By doing so, it is possible to suppress the occurrence of axial comatic aberration.

In the abovementioned first aspect, an outer diameter of the barrel may be equal to an outer diameter of the rod lens.

With this configuration, it is possible to facilitate assembly of the barrel and the rod lenses inside the same tube.

In the abovementioned first aspect, the length of the barrel may be larger than a maximum thickness of the positive lens in the longitudinal direction.

With this configuration, it is possible to further suppress tilting of the barrel and the positive lens inside the tube, thereby further suppressing the occurrence of axial comatic aberration. In addition, because an end face of the barrel protrudes farther than a lens surface of the positive lens in the optical-axis direction, it is also possible to utilize the barrel as a spacer for securing a space between the positive lens and the rod lens.

A second aspect of the present invention is a method of manufacturing a relay lens including a plurality of relay optical systems that are arranged in a long, rigid tube along a longitudinal direction and that re-form an image, wherein each of the relay optical systems includes a pair of rod lenses that are disposed with a space therebetween in the longitudinal direction, a barrel that is disposed between the pair of rod lenses along the longitudinal direction, and a positive lens that is fixed to an inner side of the barrel and that has a positive refractive power, the method including: a step of fixing the positive lens to the inner side of the barrel; and a step of processing an end face of the barrel, to which the positive lens is fixed on the inner side thereof, so as to be perpendicular to an optical axis of the positive lens.

With this aspect, after the positive lens is fixed in the barrel, the end face of the barrel is processed so as to be perpendicular to the optical axis of the positive lens. By doing so, when assembling the rod lenses and the positive lens into the tube, it is possible to determine the orientation of the barrel inside the tube in such a manner that the optical axis of the positive lens becomes parallel to the longitudinal direction of the tube merely by abutting the end face of the barrel against a flat surface of the adjacent rod lens, and thus, it is possible to manufacture a relay lens in which the occurrence of axial comatic aberration is suppressed.

A third aspect of the present invention is a method of manufacturing a relay lens including a plurality of relay optical systems that are arranged in a long, rigid tube along a longitudinal direction and that re-form an image, wherein each of the relay optical systems includes a pair of rod lenses that are disposed with a space therebetween in the longitudinal direction, a barrel that is disposed between the pair of rod lenses along the longitudinal direction, and a positive lens that is fixed to an inner side of the barrel and that has a positive refractive power, the method including: a step of fixing the positive lens to the inner side of the barrel; and a step of processing an outer circumferential surface of the barrel, to which the positive lens is fixed on the inner side thereof, so that a central axis of the outer circumferential surface coincides with an optical axis of the positive lens.

With this aspect, after the positive lens is fixed in the barrel, the outer circumferential surface of the barrel is processed so as to be coaxial with the optical axis of the positive lens. By doing so, when assembling the rod lenses and the positive lens into the tube, it is possible to determine the orientation of the barrel inside the tube in such a manner that the optical axis of the positive lens becomes parallel to the longitudinal direction of the tube merely by fitting the barrel into the tube in the longitudinal direction, and thus, it is possible to manufacture a relay lens in which the occurrence of axial comatic aberration is suppressed.

REFERENCE SIGNS LIST 1 relay lens
2 relay optical system
31, 32 rod lens
4 barrel
4a, 4b end face
4c outer circumferential surface
5, 51, 52 positive lens
6 tube
10 objective optical system
20 eyepiece optical system
30 grinding wheel
30a grinding surface
30b, 30c rotation axis
40 light source
50 detector

The invention claimed is:

1. A method of manufacturing a relay lens including a plurality of relay optical systems that are arranged in a rigid tube along a longitudinal direction and that re-form an image, each of the relay optical systems including a pair of rod lenses that are disposed with a space therebetween in the longitudinal direction, a barrel that is disposed between the pair of rod lenses along the longitudinal direction, and a positive lens that is fixed to an inner side of the barrel and that has a positive refractive power, wherein the method comprises:
    fixing the positive lens to the inner side of the barrel; and
    processing an end face of the barrel, to which the positive lens is fixed on the inner side thereof, so as to be perpendicular to an optical axis of the positive lens.

2. A method of manufacturing a relay lens including a plurality of relay optical systems that are arranged in a rigid tube along a longitudinal direction and that re-form an image, each of the relay optical systems including a pair of rod lenses that are disposed with a space therebetween in the longitudinal direction, a barrel that is disposed between the pair of rod lenses along the longitudinal direction, and a positive lens that is fixed to an inner side of the barrel and that has a positive refractive power, wherein the method comprises:
    fixing the positive lens to the inner side of the barrel; and
    processing an outer circumferential surface of the barrel, to which the positive lens is fixed on the inner side thereof, so that a central axis of the outer circumferential surface coincides with an optical axis of the positive lens.

* * * * *